Figure 1:
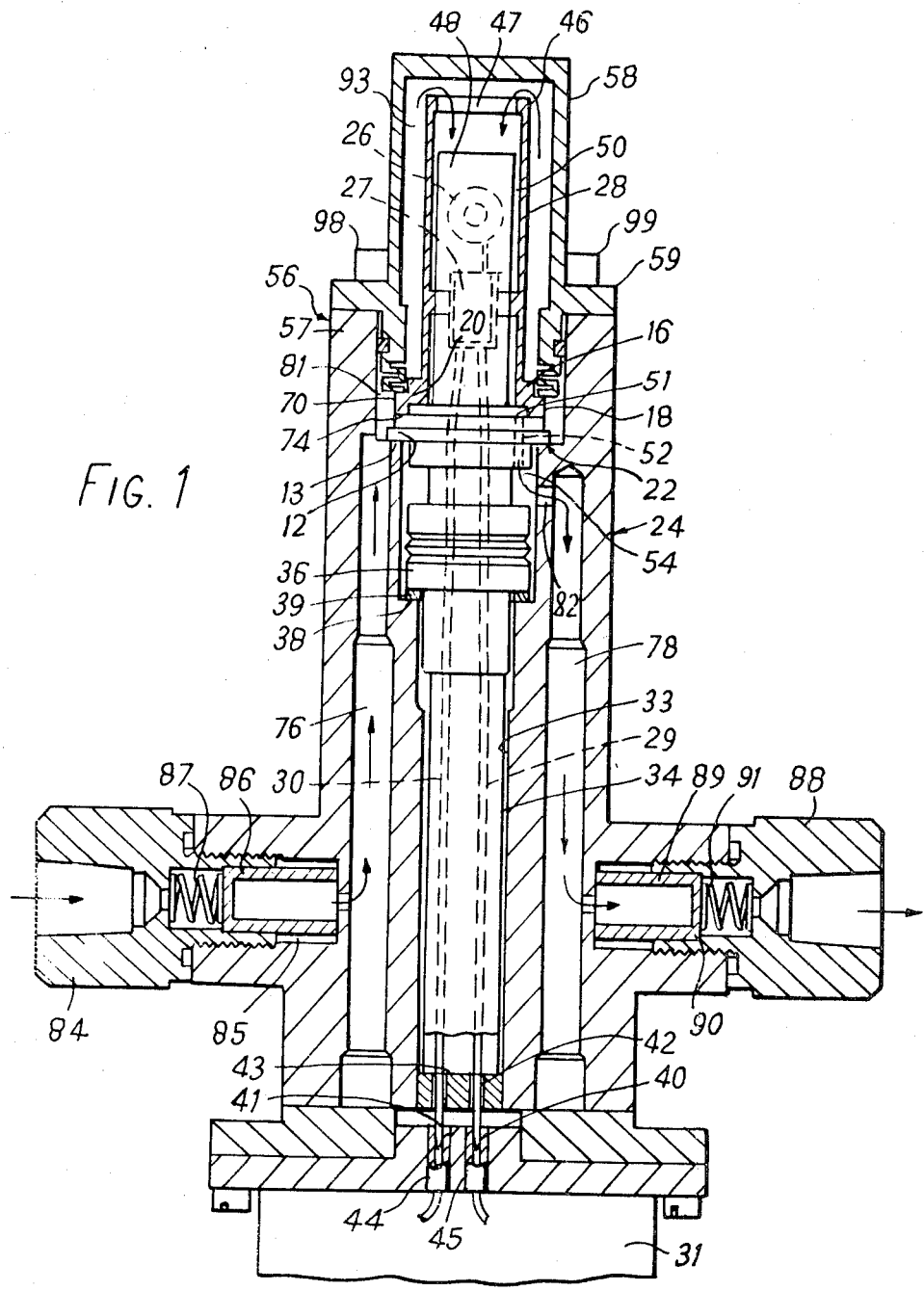

United States Patent [19]

Stansfeld

[11] 4,232,544
[45] Nov. 11, 1980

[54] TRANSDUCER FOR SENSING A PARAMETER OF A FLUID

[75] Inventor: James W. Stansfeld, Beech, Near Alton, England

[73] Assignee: Solartron Electronic Group Limited, Farnborough, England

[21] Appl. No.: 63,300

[22] Filed: Aug. 2, 1979

[30] Foreign Application Priority Data

Aug. 14, 1978 [GB] United Kingdom ............... 33229/78

[51] Int. Cl.³ .......................... G01N 9/00; G01L 9/00
[52] U.S. Cl. ....................................... 73/32 A; 73/702
[58] Field of Search ................................ 73/32 A, 702

[56] References Cited

U.S. PATENT DOCUMENTS

| 3,021,711 | 2/1962 | Arvidson | 73/702 |
| 3,585,843 | 6/1971 | Stansfeld | 73/32 A |
| 3,618,360 | 11/1971 | Curtis | 73/32 A |
| 3,774,451 | 11/1973 | Thomas | 73/702 |
| 3,874,221 | 4/1975 | Lockie | 73/32 A |

Primary Examiner—James J. Gill
Attorney, Agent, or Firm—Kevin McMahon; Dale Gaudier; Mikio Ishimaru

[57] ABSTRACT

A transducer for sensing density, pressure or pressure difference in fluids comprises a resonantly vibratable cylinder as its sensing element. The cylinder has a mounting ring at one end, the mounting ring being clamped against a base member by means of a spring arranged to exert a substantially constant clamping force on the mounting ring. An outer cover fits over the cylinder, the cover having a flange which is directly bolted to an upstanding annular rim of the base member and a depending skirt portion in which the spring is integrally formed by machining.

10 Claims, 2 Drawing Figures

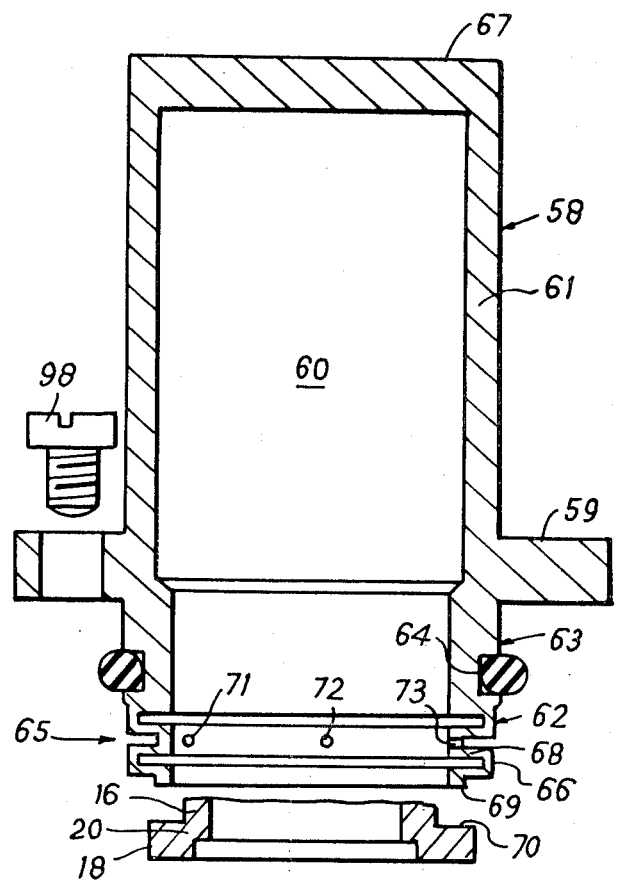

TRANSDUCER FOR SENSING A PARAMETER OF A FLUID

This invention relates to transducers suitable for use in measuring the density of or the pressure or a pressure difference in fluids, including liquids and gases.

The invention relates particularly to such transducers of the type in which there is a hollow body capable of being put into vibration and, in use, the fluid or fluids are supplied to internal and/or external surfaces of the body so that the frequency of the vibration is a measure of fluid density or pressure or pressure difference.

Known transducers of this type are described for example in U.K. Pat. No. 1,277,903, and include a generally right cylindrical hollow body, a relatively rigid base member, means for exciting natural bell-like vibration of the relatively resilient cylindrical wall of the hollow body, and means for generating a signal representative of a frequency of said vibration.

The hollow body of the transducer described in the abovementioned patent specification includes a node-forming portion, and a mounting structure connected to the node-forming portion and firmly secured to the base member, the connection of the mounting structure to the node-forming portion being elastically flexible. This way of mounting the hollow body gives very good results. However it is an object of the present invention to provide a mounting arrangement for the hollow body of such a transducer, which mounting arrangement can be used either in conjunction with, or instead of, the abovementioned way of mounting the hollow body.

According to the present invention, there is provided a transducer for measuring a characteristic of a fluid, the transducer comprising:
 at least one hollow body having a relatively resilient, resonantly vibratable, wall;
 a relatively rigid base for supporting said body;
 means for exciting resonant vibration of said relatively resilient wall;
 means for generating an output signal representative of the frequency of said vibration; and
 means for clamping said body to said base, said clamping means being adapted to produce a substantially constant predetermined clamping force between said body and said base.

The invention will now be further described, solely by way of example, with reference to the accompanying drawings, in which:

FIG. 1 is a longitudinal sectional view of part of a transducer for measuring gas density and embodying the invention; and FIG. 2 is a partially exploded sectional view of a part of the transducer of FIG. 1, but drawn to a larger scale.

FIG. 1 shows in section part of a transducer for measuring the density of a fuel gas supply or the like. The transducer includes a cylindrical hollow body 11 applied against a base member 12 by means of a mass portion within the hollow body 11. In a preferred embodiment the mass portion comprises a node-forming portion (or ring) 16 and a mounting structure (or ring) 18, the mounting structure 18 being connected to the node-forming portion 16 by means of an elastically flexible connection 20. The base member 12 is supported by means of an annular surface 13 on a first shoulder 22 within a base housing or body 24.

A drive coil 26 and a pick-up coil 27 serve as means for exciting natural vibration of the thin cylindrical wall 28 of the hollow body 11. These two coils are connected to means for generating a signal representative of the frequency of the vibration, which means are well known and essentially comprise an amplifier (not shown) having its input connected to the pick-up coil 27 and its output coupled to the drive coil 26. The amplifier is mounted in a housing 31 and is connected to the coils via four wires, two of which are indicated at 29 and 30. To permit this, the base housing or body 24 comprises a central duct 33 in which a connector pipe 34 is fitted, this pipe being coupled to the base member 12 by means of a spoolbody assembly 36, the connector pipe 34 and the spoolbody assembly 36 both surrounding the wires such as 29, 30.

The spoolbody assembly 36 sealingly engages a shoulder 38 in the duct 33 by way of an O-ring seal 39.

The connection of the coils 26 and 27 to the amplifier assembly is illustrated in FIG. 1. The four wires such as 29, 30 from the drive coil 26 and the pick-up coil 27 pass through the base member 12, the spoolbody assembly 36 and the connector pipe 34 to resepctive ones of four gold-plated pins such as 40, 41 secured in glass seals 42 in a plug 43. The four pins such as 40, 41 fit and make contact within respective ones of four gold plated sockets such as 44, 45, which comprise the four inputs of the amplifier assembly 31.

The coils 26 and 27 are arranged to operate on the thin cylindrical wall 28 of the hollow body 11 at respective anti-nodes which are equidistant from a nodal line that encircles the wall 28 in operation. Moreover, the coils 26, 27 and a part of the four wires such as 29, 30 are embedded in an epoxy resin to form a cylindrical mass 48 inside the hollow body 11.

The hollow body 11 is open at its upper end, which has an integral internal ring 46 that serves to define a nodal line encircling that end. The ring 46 is coaxial with the thin wall 28 and surrounds an inlet aperture 47 for the fluid whose density is to be measured. The internal surface of the wall 28 of the hollow body 11 and the external surface of the cylindrical mass 48 together define an annular circuit 50 extending to the base member 12, through which pass one or more of small holes 52 which communicate the annular conduit 50 with an annular space 54 defined between the spoolbody assembly 36 and the internal wall of the central duct 33.

The base body 24 has its upper end 56 an upwardly extending annular rim 57 which partially surrounds the hollow body 11. A cylindrical cover 58 has a radially outwardly projecting flange 59 which is applied against the rim 57 and fixed thereto by means of bolts such as those indicated at 98, 99.

FIG. 2 is a longitudinal sectional view of the cover 58, showing more details than were shown in FIG. 1. The illustrated cover 58 is cylindrical and made from a metal such as stainless steel, for example, the stainless steel sold by Firth Vickers under the designation S143 or FV520. The cover 58 comprises an upper casing portion 60 defined within a cylindrical wall 61 closed by a flat end face 67. The inside diameter of the cylindrical wall 61 is substantially greater than the outside diameter of the thin cylindrical wall 28 of the hollow body 11, and the height of the casing portion 60 is such that the closed end 67 is clear of the upper end of the hollow body 11 (ie the end having the ring 46) when the cover 58 is screwed on the base body 124. In fact the cover is designed so as to provide a conduit 93 for fluid or gas between the wall 61 and the closed end 67 of the cover and the hollow body 11.

The cover 58 also comprises a lower cylindrical portion 62 which meets the upper casing portion 60 in the plane of the flange 59. The lower cylindrical portion 62 includes two main parts. The first part 63 is relatively rigid, and has a groove 64 in its external surface, the groove 64 containing an O-ring which seals between the cover 58 and the internal surface of the rim 57. The second part 65 includes spring means comprising a plurality of convolutions 66 and 68.

The convolutions 66, 68 are machined in the material forming the cover 58. The annular radially-extending surface 69 of the extremity of the lower or last convolution 66 is arranged to engage an annular radially extending surface 70 of the mounting structure 18 of the mass portion 16, in much the same way as a circular obturator co-operates with a corresponding seat in a valve. It will be noted that good sealing between the surfaces 69 and 70 is not necessary, because the fluid whose density is to be measured in fact passes through the part 65 via communicating means which, in a preferred embodiment of the invention, includes a number of small apertures bored in the bottom of the convolution 68. Only three small apertures 71 to 73 are shown in FIG. 2, but typically there may be 6 or more, each with a diameter of about 1 mm.

The lower cylindrical portion 62 of the cover 58 fits inside the circular rim 57 of the base body 24, between the rim 57 and the hollow body 11, and the surface 69 of the convolution 66 clamps the mounting structure 18 onto an annular shoulder surface 74 of base member 30 surface 51. The convolutions 66,68 effectively clamp the hollow body 11 into engagement with the base member 12, and also clamp the spoolbody 36 and the seal 39 against the base body shoulder 38.

The axial length of the lower cylindrical portion 62 of the cover 58 is selected such that the spring means constituted by the convolutions 66,68 is compressed by a predetermined amount, preferably slightly beyond its elastic limit. This ensures that the clamping force exerted on the mounting structure 18 is substantially constant, and in particular, substantially independent of mechanical tolerance errors and thermal expansion effects, which results in a more stable resonance for the hollow body 11 and hence a more accurate transducer, since the forces produced by thermal expansion, for example, are not transmitted to the thin wall 28 of the hollow body 11, but are absorbed by the spring means constituted by the convolutions 66,68. In addition, this spring means applies a constant stress on the circular surface 70 all around the mounting structure 18, which stress is substantially independent on the one hand of the torque applied to the screws 98 and 99, and on the other hand of the eventual forces transmitted to the cover 58, the torque and forces being absorbed by the rim 57 of the base body 24.

With a hollow body 11 as described in the above mentioned UK patent specification, the total force provided by the annular spring means constituted by the convolutions 66,68 is about 40 kilograms when the cover 58 is completely screwed down onto the rim 57.

The base body 24 also comprises two conduits 76 and 78 respectively communicating with a space 81 between the rim 57 and the part 65 of the cover 58 and with the space 54 mentioned earlier. A fluid inlet 84 is connected by means of a filter housing 85 containing a filter 86 to the conduit 76, the filter 86 being held in its chamber by a spring 87. Likewise a fluid outlet 88 is connected by means of a filter housing 89 containing a filter 90 to the conduit 78, the filter 90 being held in its chamber by a spring 91. The conduit 78 communicates with the space 54 via an aperture 82.

The embodiment of the invention in FIGS. 1 and 2 is particularly convenient insofar as mounting, replacing or cleaning its various elements is concerned. Initially, an arrangement comprising the cylindrical mass 48 with its two coils, the base member 12, the spoolbody 36 and the connector pipe 34 containing the wires 29,30 and the plug 43 is preassembled. This sub-or pre-assembly is then fitted in the duct 33 of the base body 24, the spoolbody assembly 36 being applied against the seal 39, and the base member 12 against the shoulder 22. Next, the hollow body 11 is positioned around the cylindrical mass 48, the mounting structure 18 being applied against the shoulder surface 74. Once this lastmentioned operation has been effected, the cover 58 is bolted onto the rim 57, the extremity 69 of the spring means constituted by the convolutions 66,68 being applied against the surface 70 of the mounting structure 18. Finally, after all these operations, the amplifier assembly 31 is secured to the base body 24, the four pins such as 40,41 fitting in respective ones of the four sockets such as 44,45.

In operation, the transducer of the present invention works in a similar way to the transudcer described in the abovementioned U.K. patent specification. More particularly, in the embodiment described above, the fluid flows through the passages comprising the inlet 84, the filter housing 85 and the filter 86, the conduit 76, the space 81, the apertures 71, 72, 73, the conduit 93, the aperture 47, the space 50, the aperture 52, the space 54, the aperture 82, the conduit 78, the filter housing 89 and the filter 90, and finally exits at the outlet 88.

The passage of the fluid over the exterior of the hollow body 11 and thence to the interior of the body eliminates any pressure difference between the exterior and interior of the body 11. Consequently the wall 28 when vibrating is not affected by the pressure of the fluid, but only by the density thereof.

The spring means constituted by the convolutions 66,68 can be implemented in other ways: for example it can be implemented by providing first and second axially spaced sets of slots extending through the second part 65 of the lower cylindrical portion 62 of the cover 58, the slots of each set being equiangularly spaced around the circumference of part 65 and the slots of one set being staggered (ie angularly offset) with respect to the slots of the other set.

Although the invention has been described in relation to a vibrating cylinder density transducer, it is equally applicable to a vibrating cylinder pressure transducer.

I claim:

1. A transducer for measuring a characteristic of a fluid, comprising:
    means forming a substantially rigid cylindrical base, said means having two annular shoulder surfaces;
    a cylindrical hollow body of which a wall is relatively resilient and resonantly vibratable, said hollow body including a mounting mass structure with two annular clamping surfaces, the first of the clamping surfaces being applied against the first shoulder surface; and
    a cylindrical cover including an annular spring defined between two further annular surfaces, one of the two said further surfaces being applied against the second annular shoulder surface, and the other of the two further surfaces being applied against the second clamping surface.

2. A transducer according to claim 1, wherein said one further surface is formed on an annular flange boltable on the said second shoulder surface.

3. A transducer according to claim 2, wherein the second shoulder surface is the extremity of an annular rim or crown integral with said base, said annular rim or crown partially surrounding said hollow body.

4. A transducer according to claim 2, wherein said flange supports a cylindrical cover surrounding said hollow body.

5. A transducer according to claim 4, wherein said cover, said spring and said flange are integrally formed by machining from a single piece of metal.

6. A transducer according to claim 5, wherein said metal is stainless steel.

7. A transducer for measuring a characteristic of a fluid, the transducer comprising:
   at least one hollow body having a relatively resilient, resonantly vibratable, wall;
   a relatively rigid base for supporting said body;
   means for exciting resonant vibration of said relatively resilient wall;
   means for generating an output signal representative of the frequency of said vibration; and
   means for clamping said body to said base, wherein said clamping means forms part of a unitary cover for said hollow body, a first part of said cover including at least one resilient convolution arranged to clamp said body to said base and a second part of said cover being fixed to said base so as to compress said convolution by a predetermined amount to produce a substantially constant predetermined clamping force between said body and said base.

8. A transducer as claimed in claim 7, where said convolution includes at least one aperture for the passage of said fluid.

9. A transducer according to claim 7, wherein said convolution is machined in said unitary cover.

10. A transducer according to claim 7, wherein the cover defines a conduit for said fluid.

* * * * *